United States Patent [19]
Dornauf et al.

[11] Patent Number: 5,432,453
[45] Date of Patent: Jul. 11, 1995

[54] CARTRIDGE-SHAPED REFERENCE ELEMENT FOR PONTENTIOMETRIC MEASURING SYSTEMS

[75] Inventors: Andrea Dornauf, Kelkeim; Werner Gehringer, Darmstadt; Günter Tauber, Kriftel, all of Germany

[73] Assignee: Schott-Geräte GmbH, Hofheim/Taunus, Germany

[21] Appl. No.: 264,441

[22] Filed: Oct. 27, 1993

Related U.S. Application Data

[63] Continuation of Ser. No. 893,420, Jun. 8, 1992, abandoned.

[30] Foreign Application Priority Data

Jun. 7, 1991 [DE] Germany ............... 41 18 667.2

[51] Int. Cl.6 ............................................. G01N 27/07
[52] U.S. Cl. ................................. 324/450; 324/446; 324/722; 324/724
[58] Field of Search ............. 324/425, 439, 444, 446, 324/450, 691, 713, 715, 717, 722, 724

[56] References Cited

U.S. PATENT DOCUMENTS

| | | | |
|---|---|---|---|
| 3,601,693 | 8/1971 | Lorentzen | 324/715 X |
| 4,047,105 | 9/1977 | Anderson | 324/713 X |
| 4,427,945 | 1/1984 | Sperry, III | 324/446 |
| 4,763,065 | 8/1988 | Hachey | 324/717 X |
| 4,803,869 | 2/1989 | Barcelona et al. | 324/439 X |

FOREIGN PATENT DOCUMENTS

| | | |
|---|---|---|
| 3305962 | 8/1984 | Germany . |
| 3818846 | 6/1988 | Germany . |
| 3840961 | 6/1990 | Germany . |

OTHER PUBLICATIONS

CA114(1):2998c (abstract of JP 2120657).
Schott Geräte, Katalog 387, Kaborelektroden und Zubehör, Third Quarter, 1986, p. 19.
Schott Geräte, Katalog 3105, Elektroden für Labor und Umwelt, Fourth Quarter, 1990, pp. 30–31.
Schott Geräte, Catalog 387, Laboratory Electrodes and Accesories, Third Quarter, 1986, 5 pages.
Schott Geräte, Catalog 3105, Electrodes for the Laboratory and the Environment, Fourth Quarter, 1986, 7 pages.

*Primary Examiner*—Kenneth A. Wieder
*Assistant Examiner*—Glenn W. Brown
*Attorney, Agent, or Firm*—Millen, White, Zelano, & Branigan

[57] ABSTRACT

A cartridge-shaped reference element for potentiometric measuring systems exhibits a hollow body (20) as well as first and second sealed ends (30, 40) and a chamber (60). A silver electrode is provided as at least partial coating (50) of the inner surface of hollow body (20) bordering chamber (60), and coating (50) and protruding from chamber (60) so that a potential relating to the reference element can be measured.

18 Claims, 2 Drawing Sheets ary to prevent later corrosion of the plug-in contact. An especially careful
CARTRIDGE-SHAPED REFERENCE ELEMENT FOR PONTENTIOMETRIC MEASURING SYSTEMS This application is a continuation of application Ser. No. 07/893,420, filed Jun. 8, 1992, now abandoned.

BACKGROUND OF THE INVENTION

This invention relates in general to electroanalytical instruments, and in particular to cartridge-shaped reference elements especially useful for potentiometric measuring systems as well as a process for the production of such reference elements. For a discussion of electroanalytical measuring systems, attention is invited to the literature, for example, *Principles of Instrumental Analytics*, Third Edition, 1985, Douglas A. Skoog, Saunders College Publishing, Philadelphia, pp. 567–713, particularly pp. 600–664, as well as references cited therein directed to reference electrodes.

To produce a reliable and reproducible transition of potential between a metal conductor and an electrolyte solution, usually so-called reference elements are used. The latter are, for example, components of reference electrodes, pH glass electrodes, ion-sensitive meter electrodes or single-rod measuring systems for pH, redox, etc.

In general, the silver/silver chloride reference element is superior to the other known reference elements, such as, for example, the standard hydrogen electrode, the calomel electrode, and the Thalamid electrode. The reasons for the superiority of the silver/silver chloride reference element are: It can be used over a wide range of temperatures from about −30° C. to +135° C., it is physiologically neutral to most substances employed therewith, and the waste materials resulting therefrom can be disposed of easily.

A simple silver/silver chloride reference element consists of a silver wire immersed in a potassium chloride solution. In this connection, a thin silver chloride layer is formed on the silver electrode and a stable potential results, as long as electrical current and changing temperatures have no effect on the electrode.

The stability of the potential of such a simple embodiment is improved by saturating the potassium chloride electrolyte with an excess of silver chloride. For a further stabilization of the potential, the silver wire can be coated with a silver chloride layer either electrolytically and/or by immersion in a silver chloride melt.

For an even further improvement in the stability of the potential and especially to achieve an improved mechanical quality, silver/silver chloride reference elements are produced in cartridge form.

So-called reference cartridges consist of a thin tube and silver wire electrode, embedded in silver chloride. The tube is formed with a chamber for receiving the silver electrode and the solid silver chloride and is sealed at both ends. In this case, one end is sealed gastight and fluidtight to protect the electric connection from corrosion and the other side is sealed in a semipermeable manner to assure liquid contact with the reference electrolyte, for example the KCl solution, and to enclose the solid silver chloride in the cartridge. Such reference cartridges are known, for example, from the catalogs of the Schott Geräte Company, namely No. 387, page 19 of the 3rd quarter of 1986 as well as from no. 3105, page 30 of the IVth quarter of 1990.

In the cartridge, the gastight and fluidtight closure for protection of the electric connection is achieved by platinum wire fused onto the silver wire, to which in turn a plug-in contact can be welded for later bonding. The unit made from silver wire, platinum wire and optionally plug-in contact is fused in the area of the platinum wire in a glass tube used as an element or housing.

The process of the fusing in this case is especially expensive and critical since the platinum wire both has to be positioned for fusion and has to be guided gastight and fluidtight through the fusion point to prevent later corrosion of the plug-in contact. An especially careful treatment is required for the resulting fusion point, which has to be cooled stress-free to avoid the breaking of the glass by rapid temperature change and resultant mechanical stress.

In addition, it is known, e.g., from DT 1,303,322, that silver wire can be melted on the platinum wire instead of the plug-in contact if plug-in contact technology is unnecessary. This embodiment is just as sensitive to produce with respect to the fusion point as those mentioned above; moreover, since bonding by soldering or crimping seems to provide no special advantages, the more economical plug technology is preferred.

DE-OS 33 05 962 discloses generic, cartridge-shaped reference electrodes. In the systems described therein, a half-cell electrode in contact with the reference electrolyte and mechanically shielded toward the outside is in an inner housing, which housing contains a reference electrolyte in its electrolyte space and is connected with the inner space of an outer housing.

In DE-OS 33 05 962 there are utilized varnished silver wires, which are immersed in glass tubes and are insulated only at the end for potential formation. But this technique was not able to contribute to a better stability of the reference potential.

In addition to an electrode in wire form, planar layers of silver as a basis for a reference element have also been described, for example, in DE-PS 3,818,846. Thus, for example, CA 114(1):2998c discloses the coating of a plane substrate with a silver paste to produce electrodes for electrochemical one-time sensors (thermistors). But a design with the advantages of a cartridge for practical use thus far has not been achieved.

SUMMARY OF THE INVENTION

Relative to the above-discussed prior art, an object of this invention is to provide a cartridge-shaped reference element for potentiometric measuring systems, which is distinguished by high polarization stability and is relatively insensitive toward changing temperature changes as well as mechanical stress.

Another object is to provide a process for a clean, simple, for the most part automatable and thus reasonably priced, production of such a reference element.

Upon further study of the specification and appended claims, further objects and advantages of this invention will become apparent to those skilled in the art.

To achieve these objects, there is provided a cartridge-shaped reference element for potentiometric measuring comprising:

(a) a hollow body having an inner surface, at least one opening and one chamber containing a potential-stabilizing substance limited by sealing means and said inner surface of the body, said sealing means comprising a first sealing means semipermeable to liquids and a second sealing means which gastight and fluidtight, and (b) a silver electrode comprising an at least partial coating (50) of the inner surface of said hollow body (20) bordering said chamber (60), said coating (50) protruding from chamber (60) so that a potential can be measured with use of the reference element.

To reproduce such reference elements, a process is provided wherein:

(a) the hollow body (20) is a tube, and for the chamber (60) containing silver chloride as a potential-stabilizing substance, a first end of tube (30) is sealed in a manner semipermeable to liquids by the first sealing means (70) and the second sealing means (80) placed inside tube (20) seals tube (20) gastight and fluidtight in an axial direction, and (b) the coating (50) of the inner surface of tube (20) for the formation of the silver electrode is out of contact with the first sealing means (70) and extends up to an opposite second end (40) of tube (20).

A cartridge-shaped reference element according to the invention comprises a body having at least one opening and one chamber in its interior, and the chamber is defined by the inner surface of the body, and by a sealing means with external contact for liquids with the interior of the chamber being provided by at least one opening in the body.

By the term "body" is to be understood in the context of the invention, any arrangement or housing independent of its outer shape or its geometry, as long as said bodies or housings have a hollow space at their disposal in the interior. For example, the body can be a hollow sphere, a vessel of any geometry, or else a tube.

The designation "cartridge-shaped" in the context of the invention does not necessarily indicate a specific outer geometric shape or configuration; it rather means that the reference element is simple and safe to handle because of a sealed, encapsulated design, and is protected from outside adverse influences such as impacts or shocks. Accordingly, included in the definition of "cartridge-shaped", the reference element according to the invention, the outer shape may resemble the outward appearance of a conventional cartridge.

The chamber, a generally enclosed hollow space in the interior of the body, used for receiving a substance, which with use of the reference element then stabilizes the potential to be measured, adjoins a first sealing means on at least one point.

The first sealing means is semipermeable to liquids. According to the invention, any conventional material can be utilized, especially wadding, as well as porous plastics, natural substances, and suitable ion exchange materials. Consequently, a plurality of known and to be discovered materials can be used in principle, as long as the inner space of the chamber can come in direct intimate contact with liquids coming from the outside. There must be at least one opening in the body which will allow an external liquid to pass to a first sealing means therein, then through the latter and into the chamber. Therefore, a connection has to exist between the opening and the first sealing means.

Further, the first sealing means must not permit any potential-stabilizing substance contained in the chamber to leave the chamber as a solid due to the gravitational force of the substance, or to excessively large pores in the sealing means. All above-mentioned materials can satisfy these requirements.

The chamber further adjoins at least one other point on a second sealing means. The second sealing means must not permit either solids or gases or liquids to go through. Materials which can assure this are also conventional, for example, suitable sealing compounds based on epoxide or silicone, or other embedding compounds, as well as solder glass.

In contrast to the prior art, in which the electrode protrudes from the chamber only as wire, according to the present invention at least a part of the inner surface of the body is coated with silver. In this case, a part of the inner surface of the body, which is common to the chamber and the body, is involved. In particular, the coating has to be disposed so as to enable measurement of a potential which occurs with use of the reference element. This means that the silver coating is extended along the inner wall of the body from the chamber outward between the inner surface of the body and the sealing means, so that with connectors, clamps, wires or other conductors, a contact can be established with the extended silver layer by which a voltage can be measured.

It is not necessary that the entire inner wall of the body be evenly coated with silver. Thus, often only a partial, although continuous coating is enough; but to avoid unstable polarization, a continuous smooth coating of uniform thickness is preferred. Coating thicknesses of the inner surface of the body between 1 and 300 $\mu$m are suitable. Layers between 10 and 200 $\mu$m are preferred, particularly thicknesses between 50 and 150 $\mu$m.

Both the entire inner surface of the body bordering the chamber and the section of the inner surface of the body making contact from the first sealing means can be coated with silver to form the electrode. In this case, however, malfunctions and distortions of the potential that develop can occur, since parts of the electrode are in contact only with electrolyte solution and other parts of the electrode are in contact with electrolyte solution and a potential-stabilizing substance. Therefore, it is preferable that sections of the inner surface of the body making contact with the first sealing means exhibit no silver coating, i.e., to form a potential, electrolyte solution in each case has to penetrate through the first sealing means into the chamber.

It is further advantageous if inside the chamber, sections of the inner surface of the body proximate the first sealing means and out of contact with the latter, exhibit no silver coating. This embodiment makes it possible, in the production of the reference element, to permit larger and maintained tolerances without any reduction in the quality of the reference element.

It is advantageous, in particular for production reasons, if the body of the cartridge-shaped reference element is in the form of a tube. In this case, the chamber is formed by the inner wall of the tube and the first sealing means, which seals a first tube end and the second sealing means, which seals the second tube end.

In a cartridge-shaped reference element in tubular form, the sealing means, both the first and the second, can be placed inside the tube, so that the chamber is formed, with the extension of the tube wall projecting beyond the respective sealing means; conversely the sealing means can also be placed directly on the respective end of the tube, so that a smooth closure results on the tube ends.

But suitably a first sealing means will seal the first tube end in a semipermeable manner to liquids directly at the end, but the second sealing means will be placed in the tube interior, thus within the tube, so that the tube is tightly sealed at this point in the axial direction and is impermeable to gases and liquids.

In this case, a chamber is made inside the tube in which advantageously the coating of the inner surface of the tube for the formation of silver electrode—while omitting sections making direct contact with the first sealing means and adjoining the first sealing means—extends up to the second end of the tube.

Since the electrode in this special embodiment is guided through between the inner wall of the tube and the sealing means, it can be bonded in a very simple way. Thus, a platinum wire does not have to be fused in an expensive manner; instead a simple plug-in contact is sufficient which is plugged into the tube interior which does not belong to the chamber but is coated and thereby makes it possible to obtain the potential by clamping or optionally by attaching additional fasteners.

But it is also possible at any time, by soldering or other fastening techniques, to attach a wire or a connector, since the reference element according to the invention in its preferred tubular configuration, even if, for example, an additional soldering point is applied, is still superior to the known cartridge-shaped reference element, since the surface of the reference metal with the electrode in the form of a coating is greater than with a wire-shaped silver electrode, which results in a better stability of the potential affected by polarization.

If the second sealing means is placed directly at the end of the tube, only a possibly very small area of the silver electrode is present in coating form for bonding. But even in such a case, the derivation of a stable potential, for example by soldering on a connector or wire is still possible, if the silver coating is continued to the outer surface of the tube.

In another preferred embodiment according to the invention, the tube is made of glass. The diameter of the glass tube is about 1 to 8 mm; the diameter preferably lies in the range of 1.5 to 4 mm, especially preferably between 2 and 3 mm. All standard types of glass are suitable for production of a cartridge-shaped reference element in tubular form; solder glass in particular is also used in glass tubes as a second sealing means.

In the production of the reference element according to the invention, the process can be performed as follows:

First, a body having two opposite ends, e.g., a glass tube with a diameter of 2.2 mm, a wall thickness of 0.35 mm and a length of 110 mm, of the reference element is immersed with an open end in a coating compound, e.g., silver baking paste ARGONOR of the Doduco company, which supplies the silver for coating, of suitable viscosity.

By pressure manipulation, i.e., by slight excess pressure from outside or partial vacuum from the other side of the body, the coating compound is conveyed into the body so that at least a part of the inner surface of the body is wetted with the coating compound and/or at least a part of the inner space of the body is filled with it. The filling height, e.g., 30 mm, or the wetted inner surface can be adjusted exactly, in particular the size of the surface to be coated and the layer thickness can be controlled by the filling height.

After the desired filling height or wetting is achieved, the body is removed from the coating compound.

In doing so, a part of the coating compound remains in the inner space of the body, especially in tubular bodies, but also in other bodies of smaller cross section because of the capillary forces. But in using bodies with larger cross sections, an amount of the coating compound sufficient for coating also remains in the body because of adhesive forces.

The coating compound present in the body is then dispersed by using a gas or air stream defined by blowing or suction. By the amount of coating compound, the blowing/suction pressure and the blowing/suction time, the size and thickness of the coated surface can be controlled exactly. In the given example, the layer thickness is about 80 μm and the length of the coated surface is about 105 mm.

Then the coating is dried, e.g., at 120° C., and baked, e.g., at 520° C.; for production of a functioning reference element, a defined amount of sealing compound is subsequently introduced in the coated inner space of the body with a metering device, by which either the second open end directly or else the section of the body adjacent to the second open end is sealed gastight and fluidtight. From the second end, the coating protrudes between the sealing compound and the inner surface of the body and is accessible from the outside.

After the introduction or use of the sealing compound, the latter is permitted to dry and/or harden, and the hardening conditions such as temperature, time, moisture, etc. depend on the type of sealing compound, e.g., 24 hours at room temperature if a single-component silicone adhesive is used.

After the completion of gastight and fluidtight sealing, the potential-stabilizing substance with optional additives is filled from the non-immersed open end of the body and then suitably sealed from the same side, e.g., with wadding. Thus, the chamber is made which contains the potential-stabilizing substance.

As a potential-stabilizing substance, it is preferred to use silver chloride but silver iodide and silver bromide can also be used. In addition, other substances, known to one skilled in the art, including the conventional additives, can be introduced.

With the process according to the invention, it is especially to be emphasized that it can be completely automated, so that the reference elements including plug-in contacts can be produced automatically and so that the surface of the reference metal is not contaminated by contact during production. By clean processing, the quality of the reference element is especially improved.

In a preferred embodiment of the reference element, a thin glass tube with a diameter between about 1 and 8 mm, used as a body, is immersed in the coating compound. The use of glass tubes of this diameter assures in particular that, on the one hand, a suitable amount of coating compound remains in the tube and, on the other hand, since glass is a transparent material, so that the size of the coated surface can be optically exactly controlled and adjusted.

As coating materials, into which one end of the bodies are immersed with one end, so-called silver conductive varnishes or else silver pastes are especially suitable, as they are conventionally employed, for example, in the thick layer technology. In using glass tubes as bodies, it is further especially preferred that silver baking paste be used as coating compound. If a combination of glass tube and silver baking paste is used, a drying stage at about 100°–150° C. follows after the coating, and depending on the type of glass and paste used, a baking of silver paste then follows at about 450°–600° C.

The gastight and fluidtight sealing is produced preferably by introducing a defined amount of epoxide, silicone or solder glass as a sealing compound and then allowing the sealing compound to dry and harden. In this way, the hardening conditions depend on the type of sealing compound and in the case of the solder glass, high temperatures can also be necessary for sealing or sintering.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The entire disclosures of all applications, patents and publications, cited above and below, and of corresponding application German P 41 18 667.2, filed Jun. 7, 1991, are hereby incorporated by reference.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts/throughout the several views, and wherein.

DETAILED DESCRIPTION OF THE DRAWINGS

Figure 1:
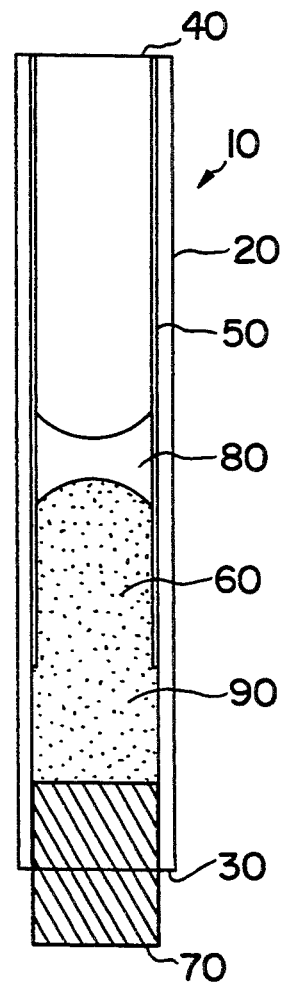
FIG. 1 is a section along the longitudinal axis of the body of an embodiment of the reference element according to the invention.
Figure 2:
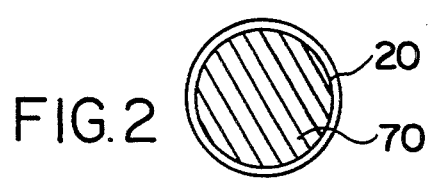
FIG. 2 is the top view from the second open end of the embodiment of the reference element shown in FIG. 1.

Reference element 10 shown in FIG. 1 comprises a hollow tube as a body 20, which has two ends 30 and 40. Tube 20 can be produced from glass, plastic or any other inert material. The inner wall of tube 20 exhibits a partial silver coating 50, which is used to form the electrode. In the example shown, coating 50 extends along the entire inner periphery of the inner wall of the tube from second open end 40 to a section at some distance from the first end of tube 20. A section of the surface of the inner wall of the tube extending from first tube end 30 in the axial direction is not coated with silver along the entire peripheral direction.

Figure 3:
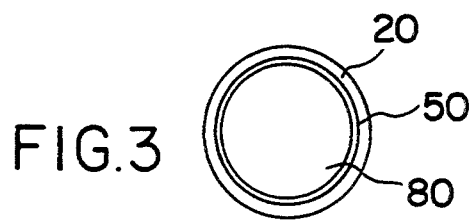
FIG. 3 is a the top view from the first open end of the embodiment of the reference element shown in FIG. 1.

In addition, body 20 exhibits a chamber 60 in its interior which is bordered by coated and non-coated sections of the inner wall of the tube as well as by first sealing means 70 and a second sealing means 80. Second gastight and fluidtight sealing means 80 is placed in the tube interior and is only in contact with coating 50 in peripheral direction of the tube, while first sealing means 70, which is semipermeable to liquids, is in contact only with the inner wall of the tube in the peripheral direction of the tube. Chamber 60, in its interior, contains a potential-stabilizing substance 90, such as, e.g, silver chloride salt, to which optionally are added also other further suitable conventional potential-stabilizing substances. As can also be seen, especially from FIG. 3, cylindrical silver layer 50 forms an electrical lead on the inner surface of the glass tube, which in the example is extended up to the second open end 40 of glass tube 20, so that the potential very easily can be picked up by a clamping contact or else a plug-in contact. Inner, metallically conducting layer 50 represents the reference metal on one side of gastight and fluidtight sealing means 80 facing chamber 60, and the larger surface offers better properties relative to the polarizability in comparison with silver wire. On the other side of gastight and fluidtight sealing means 80 facing away from chamber 60, cylindrical silver layer 50 constitutes the possibility of direct bonding with a springy connecting wire.

Below, the process according to the invention is explained in more detail using an embodiment as an example.

Figure 4:
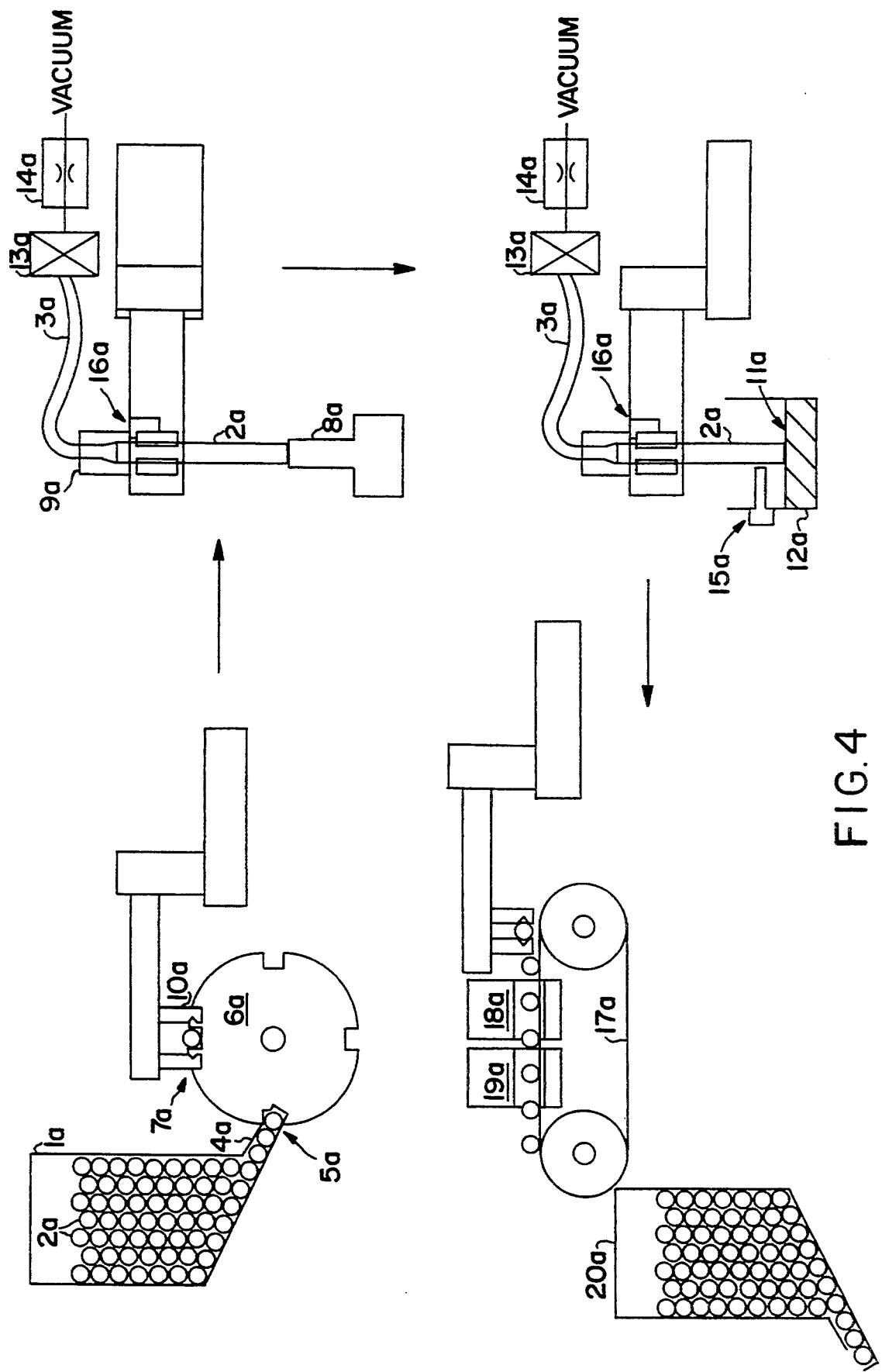
FIG. 4 a diagrammatic flow sheet of an embodiment of the process according to the invention.

As can be seen in FIG. 4, a storage chamber (1a) receives a certain number (e.g., 200 to 10,000) of glass tubes (2a). By gravitational force, an individual glass tube is brought into position (5a) along opening (4a), from which this glass tube is conveyed with a first gripping device (6a) into position (7a). From this position, glass tube (2a) is conveyed by positioning unit (8a ) to receptacle (9a), which produces the connection to a vacuum line (3a). A second gripping device (10a), which is connected with receptacle (9a), receives the glass tube and conveys it into position (11a), in which one end of glass tube (2a) is immersed in silver coating paste (12a). A defined partial vacuum in glass tube (2a) by the second end is produced by valve (13a) and a throttle (14a), so that coating paste (12a) is sucked into glass tube (2a).

An optoelectronic sensor (15a) detects and signals the achieved filling height and controls valve (13a), throttle (14a) and gripping device (10a) to remove the glass tube from the coating paste and to disperse coating paste (12a) in glass tube (2a) by using a vacuum at one end of glass tube (2a) and the outside air pressure and to coat the inner surface of the glass tube with paste (12a). As an alternative to using the vacuum, to disperse the coating paste, the glass tube also can be connected with the second end with a fitting for blowing, not shown. A second optoelectronic sensor (16a) detects the specified length of the inner surface of glass tube (2a) to be coated and turns off the vacuum by valve (13a), by which the surface of the glass tube to be coated is determined exactly.

Second gripping device (10a) conveys glass tube (2a) onto a conveyor belt (17a), which conveys the glass tube first through drying furnace (18a), then through a baking furnace (19a), then to be deposited in second storage chamber (20a). In a way similar to the above-described coating of the inner surface of the glass tube with silver coating paste, the metering of the epoxide resin to form second sealing means (80) also takes place for protection against corrosion of the connecting contact.

The filling of chamber (60) with potential-stabilizing silver chloride and additives as well as attaching first sealing (70) can be conducted conventionally.

Thus, a completely novel method is described for the production of reference elements for potentiometric measuring systems. The thus-produced reference cartridges have both technical and economic advantages relative to the conventionally produced reference cartridges.

The entire disclosure of all applications, patents and publications, cited above and below, and of corresponding German Application P 41 18 667.2, filed Jun. 7, 1991, are hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A cartridge-shaped reference element for potentiometric measuring comprising:
   (a) a hollow body having an inner surface, at least one opening and one chamber (60) containing a potential-stabilizing substance (90), said substance being confined within said chamber (60) by a first and second seal and said inner surface of the body, said first seal being semipermeable to liquids and said second seal being gastight and fluidtight, the second seal being located in the hollow body such that a portion of the inner surface of the hollow body is not bordering the chamber and not covered by a seal, and
   (b) a silver electrode comprising an at least partial coating (50) of the inner surface of said hollow body (20) bordering said chamber (60), said coating (50) contiguously extending from the inner surface in said chamber (60) along at least part of the inner surface covered by the second seal and to at least part of the portion of the inner surface of the hollow body not bordering the chamber and not covered by a seal,
   whereby a potential may be measured with use of the reference element.

2. A cartridge-shaped reference element according to claim 1, wherein sections of the inner surface of the hollow body (20) in contact with the first seal (70) exhibit no silver coating.

3. A cartridge-shaped reference element according to claim 2, wherein, sections of the inner surface of the hollow body (20) adjoining first (70), not contacted by the latter, exhibit no silver coating.

4. A reference element according to claim 2, wherein the entire inner surface of the hollow body, with the exception of the inner surface in contact with the first seal, is silver-coated.

5. A cartridge-shaped reference element according to claim 1, wherein the thickness of the coating (50) of the inner surface of hollow body (20) is between 1 and 300 μm.

6. A cartridge-shaped reference element according to claim 5, wherein the thickness of the coating (50) of the inner surface of hollow body (20) is between 10 and 200 μm.

7. A cartridge-shaped reference element according to claim 5, wherein the thickness of the coating (50) of the inner surface of hollow body (20) is between 50 and 150 μm.

8. A reference element according to claim 1, wherein the body (20) is glass.

9. A reference element according to claim 8, wherein the diameter of the glass body is 1–8 mm.

10. A reference element according to claim 8, wherein the diameter of the glass body is 1.5–4 mm.

11. A reference element according to claim 8, wherein the diameter of the glass body is 2–3 mm.

12. A cartridge-shaped reference element according to claim 1, wherein:
    (a) the hollow body (20) is a tube, said potential stabilizing substance (90) comprises silver chloride, a first end (30) of tube (20) is sealed in a manner semipermeable to liquids by the first seal (70) and the second seal (80) placed inside tube (20) seals tube (20) gastight and fluidtight in an axial direction, and
    (b) the coating (50) of the inner surface of tube (20) for the formation of the silver electrode is out of contact with the first seal (70) and extends up to an opposite second end (40) of tube (20).

13. A reference element according to claim 12, wherein the entire inner surface of the tube, with the exception of the inner surface in contact with the first seal, is silver-coated.

14. A reference element according to claim 1, wherein the hollow body is a tube having two openings and the second seal is located within the tube removed from an opening such that a circumferential section of the inner surface which does not border the chamber and is not covered by the seal extends into the tube.

15. A reference element according to claim 14, wherein the entire circumferential section of the inner surface extending into the tube, which does not border the chamber and is not covered by the seal, is silver-coated.

16. A reference element for potentiometric measuring comprising:
    a hollow body having an inner surface at least partially coated with a silver electrode, first and second openings, a first seal semipermeable to liquids, a second seal which is gastight and fluidtight and a potential-stabilizing substance,
    wherein, the hollow body is sealed against the first opening by said first seal and against the second opening by said second seal, such that a chamber is defined in the hollow body by the at least partially coated inner surface and said two seals, and the potential-stabilizing substance is confined within said chamber,
    wherein the second seal is located within the hollow body such that a portion of the at least partially coated inner surface between the second seal and the second opening is exposed, and,
    wherein at least a part of said silver electrode coating contiguously extends from the inner surface bordering the chamber to the exposed portion of the at least partially coated inner surface between the second seal and the second opening.

17. A reference element according to claim 16, wherein no part of the inner surface contacting the first seal is coated with the silver electrode.

18. A reference element according to claim 17, wherein the entire inner surface of the hollow body, with the exception of the inner surface in contact with the first seal, is coated with the silver electrode.

* * * * *